United States Patent [19]

Larson

[11] 4,198,161

[45] Apr. 15, 1980

[54] LOW TURBIDITY NEPHELOMETER

[75] Inventor: Paul E. Larson, Fort Collins, Colo.

[73] Assignee: Hach Chemical Company, Loveland, Colo.

[21] Appl. No.: 881,569

[22] Filed: Feb. 27, 1978

[51] Int. Cl.² ............................................. G01N 21/22
[52] U.S. Cl. .................................... 356/339; 250/574
[58] Field of Search ............... 356/337, 338, 340, 339, 356/342; 250/574

[56] References Cited

U.S. PATENT DOCUMENTS 3,364,812  1/1968  Ewing .................................. 356/103
4,118,625  10/1978  Underwood ..................... 356/339 X Primary Examiner—John K. Corbin
Assistant Examiner—Bruce Y. Arnold
Attorney, Agent, or Firm—Leydig, Voit, Osann, Mayer & Holt

[57] ABSTRACT

An improved nephelometer comprised of a transparent cell for containing a liquid sample, a light source, and a detector is disclosed which reduces the amount of stray light reaching the detector. The cell is characterized in that either the illuminating light beam or the detected light passes through the cell wall face at an acute angle to the normal to the cell wall face.

1 Claim, 3 Drawing Figures

LOW TURBIDITY NEPHELOMETER

This invention relates generally to turbidimeters and more particularly concerns a nephelometer suited for low turbidity levels.

A nephelometer measures the turbidity of a water sample by directing a beam of light into the sample and sensing the light scattered, usually at right angles, from particles of turbidity suspended in the water. When low levels of turbidity are sought to be sensed, the presence of stray light in the instrument becomes more and more critical.

It is conventional to contain the sample in a glass cell through which the exciting light beam and the reflected light pass. Refraction, reflection and scattering of the light all contribute to stray light affecting the sensitivity of the instrument.

It is the primary aim of the invention to provide a nephelometer with very low stray light characteristics. A further object is to provide such a nephelometer without added cost or creating cleaning problems.

Other objects and advantages of the invention will become apparent upon reading the following detailed description and upon reference to the drawings, in which.

Figure 1:
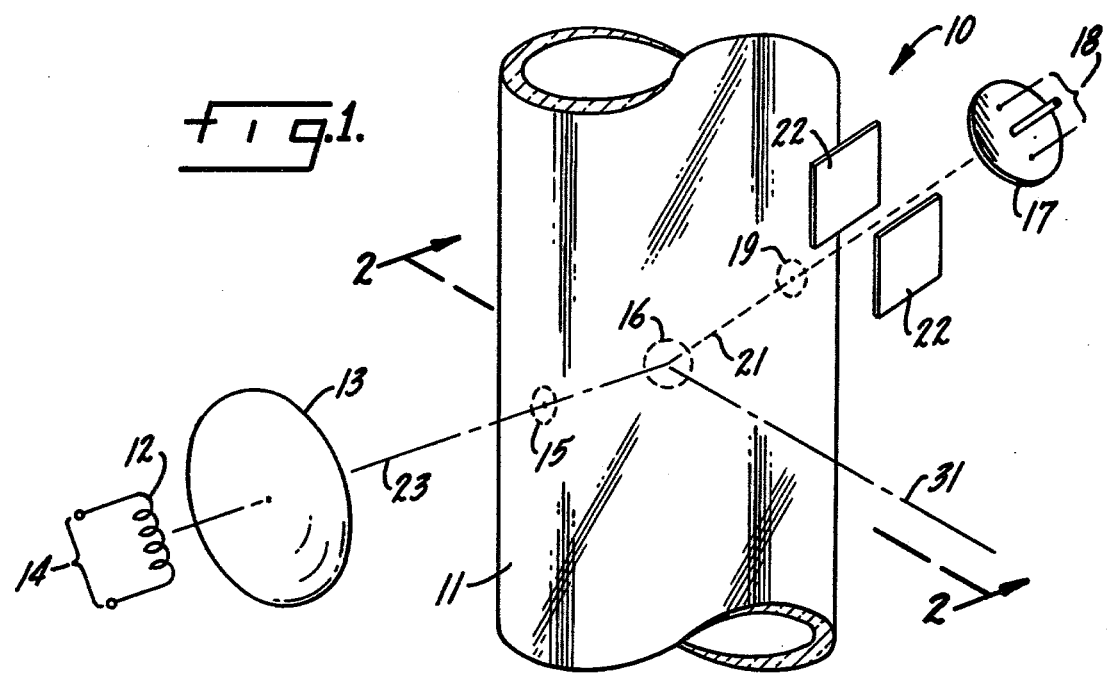
FIG. 1 is a fragmentary schematic perspective of the elements of a nephelometer embodying the invention.
Figure 2:
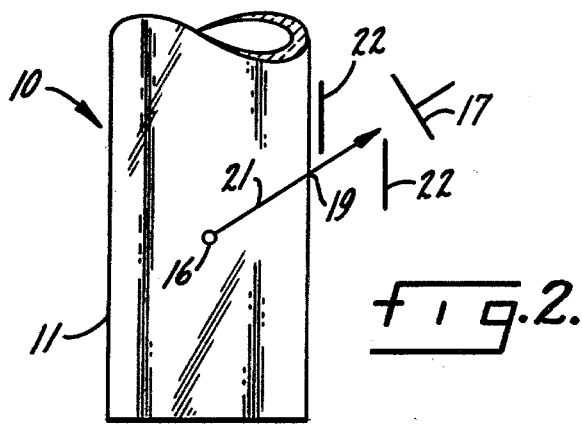
FIG. 2 is a schematic elevation taken approximately along the line 2—2 in FIG. 1.

While the invention will be described in connection with a preferred embodiment, it will be understood that I do not intend to limit the invention to that embodiment. On the contrary, I intend to cover all alternatives, modifications and equivalents as may be included within the spirit and scope of the invention as defined by the appended claim.

Turning to the drawings, there is diagrammatically shown a nephelometer 10 having a cylindrical glass cell 11 containing the water sample, a light source 12 and a lens 13. The light source 12 is connected to a source of power 14 for focusing a beam of light through the cell wall at 15 to illuminate a region 16 in the center of the cell 11. A light detector 17 is coupled to a suitable circuit 18 for sensing light scattered from turbidity particles in the region 16 through the cell wall at 19 along a scattered light path 21. A pair of shields 22 partially protect the detector 17 from unwanted light. As is conventional, the light beam center line 23 and the scattered light path 21 are at right angles.

In accordance with the invention, the cell 11 is sharply angled with respect to the plane of the light center line 23 and the scattered light path 21 so that light does not both enter and leave the cell perpendicularly to the cell walls. That is, only the region 15 is perpendicular to the cell wall face while light passing through the region 19 is not perpendicular to the cell wall face. The same effect can be reached by tilting the cell in the direction to make the region 15 non-perpendicular and allowing the region 19 to be perpendicular to the cell wall, in other words, to angle the light beam center line 23 into the cell rather than have the reflected light path 21 angled out of the cell.

Figure 3:
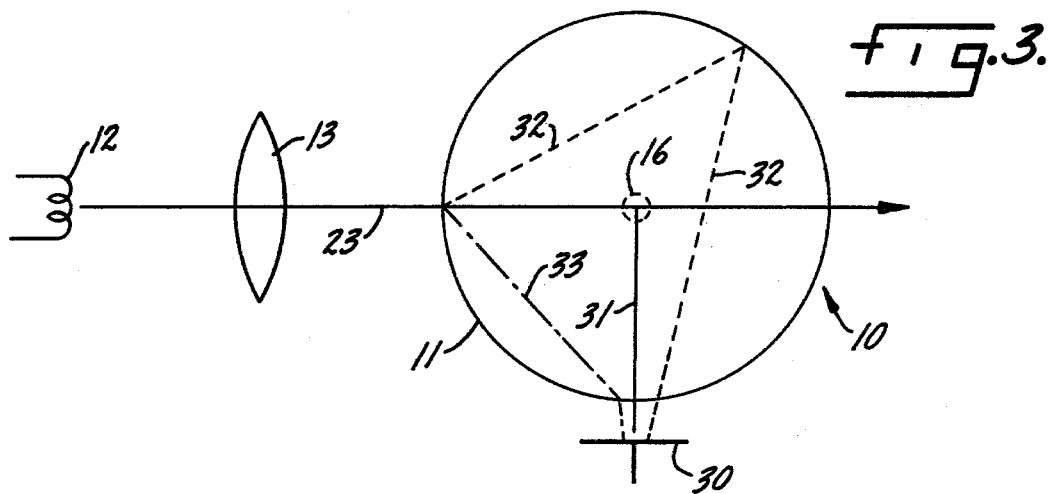
FIG. 3 is a diagram illustrating the basis of the invention and showing what would be a horizontal section of the instrument with an alternate positioning of the parts.

This seemingly simple modification of the basic nephelometer design dramatically reduces the amount of stray light reaching the detector. The explanation lies in the discovery that far more light, on the order of 400 times more, reaches a detector after being reflected perpendicularly to the inner faces of the cell wall than after being refracted and scattered by the cell walls. This is illustrated in FIG. 3 where a detector 30 has been positioned along a center line 31 (see FIG. 1), that is, at right angles to the center line 23 and perpendicular to the walls of the cell 11. In that position, the detector 30 will receive much more reflected light as via the path 32 than scattered light as along the path 33. By keeping the sensing reflected light path out of the plane of the light reflected from the inner walls of the cell, the amount of stray light reaching the detector is greatly reduced.

This advantage is achieved in the nephelometer 10 with virtually no increase in cost or complexity, and without creating a cleaning problem as can result from complicating the shape of the sample containing cell. The invention is well suited for dual beam instruments in which transmitted light is also detected and compared with reflected light since the side of the cell opposite the light source 12 remains open for a transmitted light sensor.

I claim as my invention:

1. In a nephelometer, the combination comprising, a transparent cell for containing a liquid sample, a light for directing a beam of light into said cell, and a light detector positioned to receive light scattered at right angles from a region in the cell illuminated by said beam, said cell characterized in that either the illuminating light beam or the detected light passes through the cell wall face at an acute angle to the normal to said cell wall face.

* * * * *